United States Patent [19]
Maget et al.

[11] Patent Number: 5,938,640
[45] Date of Patent: Aug. 17, 1999

[54] TWO-PART FLUID DISPENSER

[75] Inventors: Henri J. R. Maget, La Jolla; Donald H. Koenig, San Diego, both of Calif.

[73] Assignee: M&R Consulting Services, San Diego, Calif.

[21] Appl. No.: 08/869,769

[22] Filed: Jun. 4, 1997

[51] Int. Cl.$^6$ .................................................. A61M 37/00
[52] U.S. Cl. ......................................... 604/145; 604/131
[58] Field of Search ..................................... 604/130–146

[56] References Cited

U.S. PATENT DOCUMENTS

| | | |
|---|---|---|
| Re. 35,501 | 5/1997 | Ross et al. .............................. 604/141 |
| 3,894,538 | 7/1975 | Richter . |
| 4,402,817 | 9/1983 | Maget . |
| 4,522,698 | 6/1985 | Maget . |
| 4,902,278 | 2/1990 | Maget et al. . |
| 5,242,565 | 9/1993 | Winsel . |

*Primary Examiner*—Wynn Wood Coggins
*Assistant Examiner*—Deborah Blyveis
*Attorney, Agent, or Firm*—Brown, Martin, Haller & McClain

[57] ABSTRACT

A fluid dispensing device is disclosed which has interfitting pump and reservoir modules, with unique releasable tight-fitting coupling mechanism incorporated into the opposed surfaces of the modules. Use of the two interfitting modules permits repeated re-use of the pump module containing the permanent electrical component, with a plurality of seriatim reservoir modules. Only the reservoir module needs to be sterilized. The battery power for the pump can come from a battery positioned within the pump module, which may be used with two or more reservoir modules, or within each reservoir module, which is used only with that single reservoir module. Pumping rate may be fixed or controllable. The coupling mechanism can be central of the device or off-center and is manually operable. The device may be used to provide medications, prophylactics, hormones, drugs, other treating agents for disease or dysfunction, vitamins, minerals, dietary supplements, biological compositions, fragrances, insecticides or vaporizable compounds which mask or eliminate undesirable odors in the ambient environment.

20 Claims, 3 Drawing Sheets

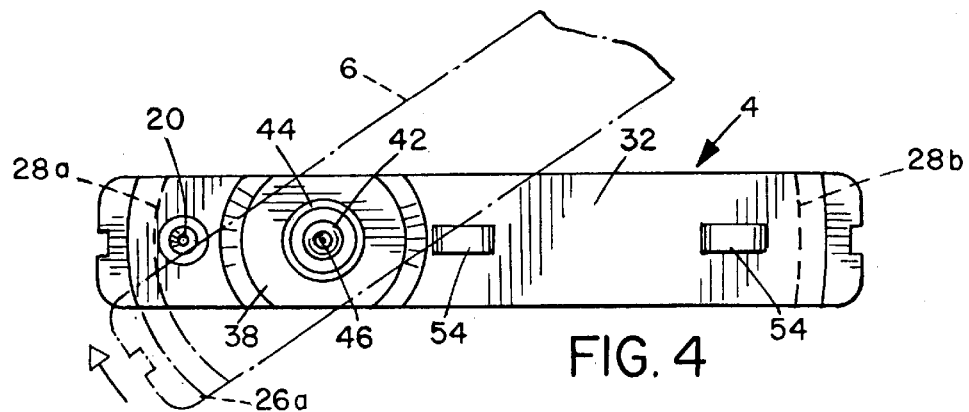
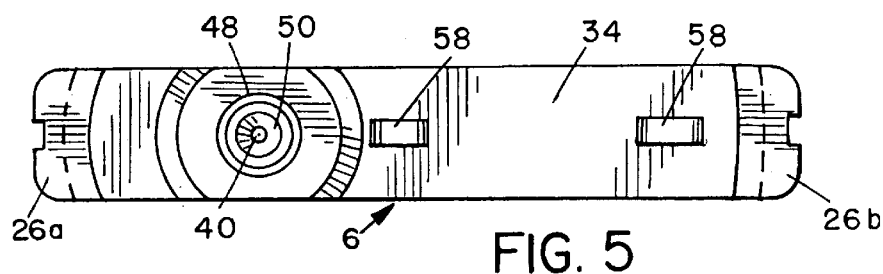
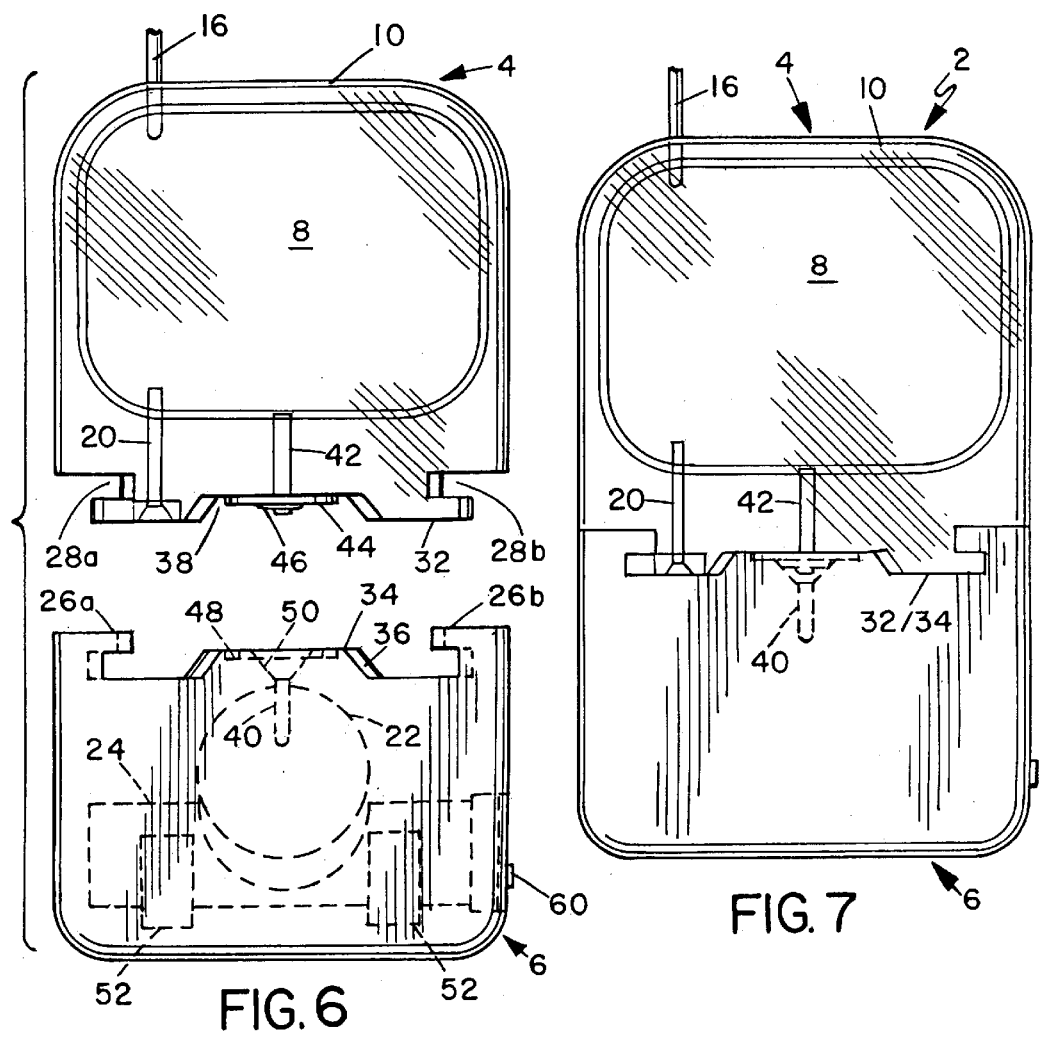

TWO-PART FLUID DISPENSER

BACKGROUND OF THE INVENTION

1. Field of the Invention

The invention herein relates to fluid dispensing devices. More particularly it relates to small, portable fluid dispensing devices, including devices used to dispense metered quantities of liquid medication to ambulatory patients and devices to disperse vapors into the surrounding environment.

2. Description of the Prior Art

In recent years there have been numerous applications for small, easily portable liquid and other fluid dispensers. A major application for instance, is in the medical and veterinary fields, where ambulatory patients, whether human or animal, can wear or carry such devices which are used to administer medication to them on an ongoing or extended basis.

Another use of such devices is to provide for dispersion of gases or vapors into the ambient environment. Typical for instance, are the small vapor dispensing devices used in homes and offices to provide either a pleasant scent or to mask or eliminate undesirable odors.

Many of the previous devices have been single use products. The devices supplied with a sufficient quantity of a propellant to force the liquid in the reservoir to be ejected from the device over a predetermined time period. Once the quantity of liquid is dispensed, the propellant is substantially used up and the device is simply discarded. Successful attempts to reuse such devices by refilling and recharging have been of only limited success, since the difficulty of such refilling and recharging is usually sufficiently great that it is more economical to discard the device and simply provide a new device with a new quantity of liquid and a new propellant charge.

A number of small portable electrochemical dispensing devices have previously been developed which can continually dispense liquid at preset or controllable rates. The devices use novel electrochemical pumps which have been the subject of prior United States patents, including U.S. Pat. No. 4,902,278 to co-applicant Maget entitled "FLUID DELIVERY MICROPUMP," in which electrochemistry and membrane technology is used to reduce oxygen in air on one side of a water-containing electrolytic cell and oxidize oxygen from the water on the opposite side to generate molecular oxygen, with the molecular oxygen so generated being used as the propellant to force liquid from an adjacent reservoir. A variety of different types of devices have been developed and patented and others are the subject of pending patent applications. All of these devices however, have either been single unit devices in which the pumping mechanism was integral with the reservoir structure or, for those devices where the pumping mechanism was separable from the liquid or gas reservoir portion, the devices have been such that the coupling between the two portions was rudimentary and the devices were not designed for more than limited portability.

SUMMARY OF THE INVENTION

The devices of the present invention overcome the limitations of the prior art while retaining all of the benefits of the prior art devices. There is an easily fillable reservoir portion, and a compact pump and electronics portion so that the novel electrochemical pumps previously mentioned can be used. Because of the unique coupling mechanism used in the present invention, the reservoir and the pump/electronics component or module can be easily separated from the reservoir portion or module, but when in use will remain tightly sealed with provision for the interconnections necessary to operate the device. Since the two portions or modules of the device are constructed with mating coupling mechanisms, the pump/electronics module can be attached to a series of reservoir modules, such that the fresh reservoir modules can be used in sequence while maintaining a single pump/electronics module which has a much longer service life than any of the reservoir modules.

Another important advantage of the coupled module devices of the present invention is that the electrical and pumping components will be housed in a separate module which will not need to or be subject to sterilization, which can have an adverse effect on many electronic components. Only the reservoir module will be subject to sterilization. If desirable, the two modules can be housed in casings of different but compatible materials, with the casing of the reservoir module being of a material which is not harmed by the sterilization procedure, and the casing of the pump module being of a material for which such inertness to sterilization is not a factor.

The electrical power for the device is normally provided by one or more batteries, and commonly will use the ordinary commercial batteries used for flashlights, radios, hearing aids, calculators and other small electronic devices. The battery or batteries can conveniently be included in the pump module, especially for those devices where the pumping requirements are such that battery life is expected to be substantially longer than the service life of a one or a few filled reservoirs. In a particularly preferred and unique configuration however, this invention also includes an embodiment where a battery (or batteries) is enclosed in the reservoir module and there are interconnecting electrical contacts which are closed when the two modules are secured together by the coupling mechanism. This is particularly useful when the pumping requirements and amount of fluid in the reservoir are such that a fresh battery is expected to be needed each time the reservoir is emptied and needs to be replaced. By including the battery directly in each reservoir module, interchange of modules with the single pump module becomes quite simple and the user need never worry about a battery having to be changed or a battery being discharged prior to completion of pumping of the fluid from each reservoir.

The devices are conveniently made with housings of metal, plastic or similar common and inexpensive materials. In a particularly preferred embodiment, at least a portion of the wall of the reservoir module will be transparent, so that the quantity of liquid in the reservoir can be visually ascertained at any time.

It will also be preferred to include capability for the device to be easily attached to various types of medical administration devices, such as IV needles, cannulas, transdermal patches, or the like, for those devices which are intended to administer medication to the user.

Among the materials which may be provided or administered are medications, prophylactics, hormones, drugs, other treating agents for disease or dysfunction, vitamins, minerals, dietary supplements, biological compositions, fragrances, insecticides or vaporizable compounds which mask or eliminate undesirable odors in the ambient environment.

In many embodiments, the device will include variable controls, such that the pumping rate of the pump module can be varied, either continuously as with a rheostat or potentiometer control, or in discrete steps as with a multipole switch, so that the amount of medication, fragrance or other liquid or vapor can be varied by the user to obtain the correct degree of dispensing under the given circumstances.

BRIEF DESCRIPTION OF THE DRAWINGS

FIG. 4 is a bottom plan view of the reservoir module of the device, with the mode of attachment of the pump module to the reservoir part indicated in phantom lines;

FIG. 5 is a top plan view of the pump module of the device;

FIG. 6 is a front elevation view of another embodiment of a device of this invention, with the reservoir and pump modules thereof shown in separated position and certain internal components indicated;

FIG. 7 is a front elevation view of the device of FIG. 6, with the parts in joined configuration;

DETAILED DESCRIPTION AND PREFERRED EMBODIMENTS

The invention is best understood by reference to the drawings. With reference to embodiments as illustrated in the Figures the relative terms "upper," "lower," "above," "below," "top," bottom" and the like will be used. It will be understood, however, that these are used only to enhance understanding of the Figures, and that the actual devices of this invention may be used in any spatial orientation.

Figures 1, 2, 3:
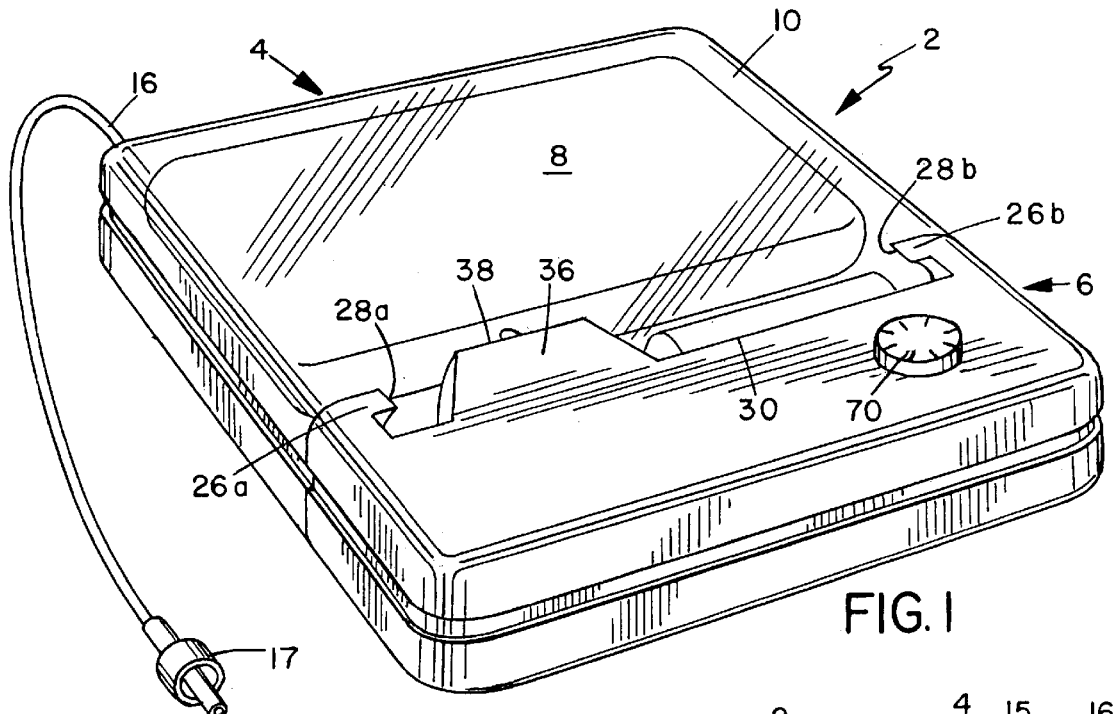
FIG. 1 is a perspective view of one embodiment of a device of this invention.
FIG. 2 is a front view of the device of FIG. 1, with the reservoir and pump modules thereof shown in separated positions and certain internal components indicated.
FIG. 3 is a cross-sectional view of the device taken on line 3—3 of FIG. 2.

FIG. 1 illustrates a typical embodiment of the invention in the closed configuration with the two modules or portions joined. The overall device 2 is made up of the reservoir portion or modules 4 and the pump or pump/electronics portion or module 6. As best seen in FIGS. 2 and 3, the reservoir module is substantially a housing for an enclosed chamber 8. The outer housing 10 of the reservoir module 4 defines the maximum volume of the chamber 8. Within the chamber 8 is a fluid containment reservoir 12 which holds the liquid, vapor or other fluid composition which is to be dispensed from the device 2. Preferably reservoir 12 is formed by a gas- and liquid-impermeable flexible thermoplastic film 11 which conforms to a portion of the interior surface of the chamber 8, generally the bottom and one, two, or preferably three sides of the chamber 8. The film 11 will be sealed at its edges to the interior surface of the chamber 8, such that the reservoir 12, formed by the film and the remaining exposed inner surface area 19 of the chamber, will initially substantially fill the entire chamber 8. Between the film 11 and the film-covered portion of the bottom and inner side surfaces of the chamber 8, however, there will be a small gas-filled space 14 initially present, since the film is not attached to the covered portion of the bottom or side surfaces except at the film's edges. The initial gas in space 14 is usually air, but it may be an inert gas such as nitrogen or argon if desired. It is into space 14 that the motivating gas pumped from pump 22 will eventually flow, with the pressure of the motivating gas generated by pump 22 causing the film 11 to move toward exposed wall surface 19, thus collapsing reservoir 12 and forcing the contained fluid 18 out of the device through outlet port 16. As the operation continues, space 14 will enlarge, the film 11 will move further toward wall surface 19, and the reservoir 12 will compress until substantially all of the fluid 18 within the reservoir 12 have been expelled and film 11 is adjacent wall surface 19. As will be noted below, the advantage of this embodiment is that at least outlet port 16 may be formed in the housing 10 rather than having to penetrate the film 11 to form fluid communication with reservoir 12.

Alternatively, reservoir 12 may be configured as a bag having continuous flexible but liquid or gas impermeable walls 13 and 13' (wall 13 in FIG. 2 being shown as co-extensive with film 11 and the remainder of the bag wall, designated 13', being shown in phantom). Typically, the bag wall 13/13' will be formed of a rubber or elastomeric material so that the overall bag is compliant with the interior shape of the chamber 8.

The housing 10 is relatively rigid, to the extent that hand pressure alone will not cause it to flex or depress sufficiently to expel fluid from within the reservoir 12. The rigid walls of housing 10 will retain the gas pressure within chamber 8.

There will normally be one port in the reservoir 12, outlet port 16. In many cases outlet port 16 may also be used initially for filling the reservoir 12 with the fluid 18 to subsequently be dispensed. Alternatively, however, there may be an optional separate inlet port 20 which is intended to be used only once, to fill the reservoir 12, after which it may be sealed. As noted above, in the preferred film 11 embodiment of the reservoir 12, the outlet port 16 is formed in housing 10 so as to open directly into the reservoir 12 space, as indicated at 15. Outlet port 16 will normally be initially closed by a septum or valve and will be activated only by the increased fluid pressure provided by the inflow of the motivating gas into the space 14, and not merely by the normal static pressure of the fluid 18 in the reservoir. If a valve is present, it may be a flap valve, a small spring-loaded ball valve, or the like unidirectional valve.

If inlet port 20 is present, preferably it will be an elastomeric septum in which is pierced by a hollow needle to fill the reservoir 12, and then is essentially self-sealing when the needle is withdrawn. The needle will penetrate the film 11, but that also will be self-sealing when the needle is withdrawn. Alternatively, the port 20 may initially be open for machine filling and then sealed as by a septum or stopper. In yet another embodiment, if the reservoir module 4 is intended to be recycled and refilled for later use, the inlet port 20 may be closed using an openable closure rather than permanent seal. While both inlet port 20 and outlet port 16 are shown as straight conduits, either may if desired be formed in curved, angles or other shapes. For instance, inlet port 20 could include an angled offset so that it enters reservoir 12 through exposed wall 19, so that there is no need to penetrate the film 11. Inlet port will either be sealed or be unidirectional, so that internal pressure within reservoir 12 will not open it.

Where the reservoir is formed as a bag with walls 13/13', the degree of flexibility of the walls 13/13' will determine the preferred type of ports 16 and 20 used. If the wall material is relatively stiff, the ports may be elastomeric septa in the wall. If the wall material is relatively more flexible, the ports may incorporate valves as described above, which may have to be located externally of the bag.

It is preferred, as illustrated in FIGS. 1–3, that the outer housing 10, or at least a portion thereof, be made of a transparent material, such as a clear plastic, so that the condition of the reservoir 12 inside and thus of the fluid content of the reservoir, can be readily observed visually merely by looking at the device. It may also be desirable to have the reservoir 12 itself be formed of a clear flexible plastic material so that the liquid or vapor inside can be observed directly. This will be particularly advantageous if the liquid or vapor 18 has a color rather than being a clear liquid or gas. It is not necessary that the entire outer housing 10 be made of a transparent material; rather, only one side (e.g., the exposed side 19) or a "window" of clear material could be used with the remainder being translucent, colored or otherwise opaque. In some cases this may also be desirable because it would allow one to view the condition of the reservoir 12 through a clear side of the housing 10 but see it against a colored or dark background which would contrast with the appearance of the reservoir.

The pump module 6 is a housing which includes the pump 22 and the various electronic control and circuitry elements generally indicated at 24. The placement of the pump 22 and the electronic components 24 will be merely a matter of choice and convenience which will depend on the configuration of the device 2 and particularly the pump module 6. Specific details will be described below.

The opposite facing ends of the reservoir module 4 and the pump module 6 will be configured so as to form a tight fitting but releasable coupling mechanism with a direct connection between the pump and the space 14.

While there may be other types of couplings which are useful, we prefer to use a sliding tongue and groove structure best illustrated in FIGS. 2 and 4. In the embodiment shown, the pump module 6 is fitted with undercut curved flanges 26a and 26b. These interfit with an interference fit into grooves 28a and 28b, respectively, in the reservoir housing 10. The dimensions and configuration of the respective pairs of flanges and grooves 26a/28a and 26b/28b are such that the user can turn the two modules 4 and 6 against each other as indicated in FIG. 4 without undue force, but the interference fit between the respective flanges and grooves will be such that a tight fit between the two modules is obtained. The joint 30 between their opposite faces 32 and 34 may be close with the intent of excluding dust, dirt and liquids and other contaminants. It is preferred, however, that there be a small amount of clearance between surfaces 32 and 34 to facilitate the sliding rotational motion when the two modules 4 and 6 are joined or separated.

Figure 8:
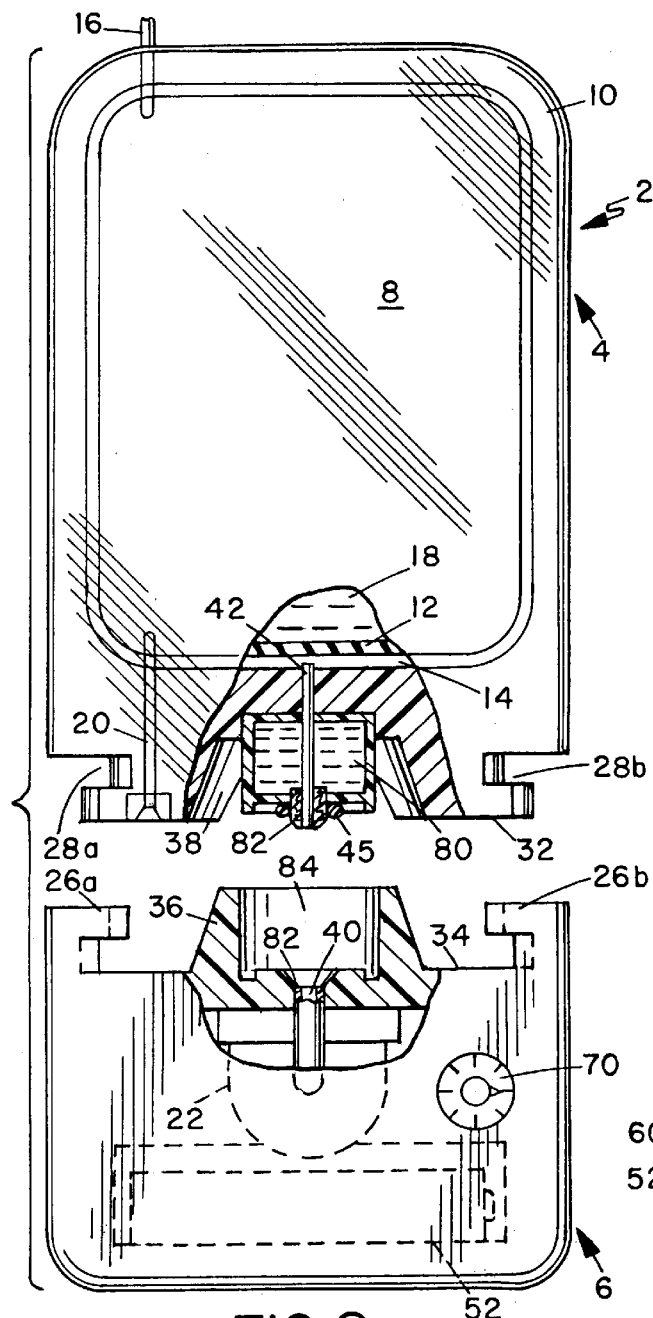
FIG. 8 is a front elevation view of yet another embodiment of a device of this invention, with the reservoir and pump modules thereof shown in separated position and certain internal components indicated.

The reservoir module 4 and pump module 6 will have mating means on their opposed surfaces 32 and 34 to provide for fluid communication of the gas from the pump 22 into the space 14 surrounding the reservoir 12 within the housing 10 of the reservoir module. In the embodiment shown in FIGS. 2 and 3, the mating mechanism comprises a raised boss 36 on surface 34 of module 6 and a corresponding recess 38 in surface 32 of module 4, with both the boss 36 and recess 38 being in the form of truncated cones to fit together in male:female fashion and still can be rotated as indicated in FIG. 4. Within the boss 36 is a fluid conduit 40 which leads to the outlet of pump 22 and provides for passage of the pump gas from the pump 22 to the top surface of boss 36. Aligned with and opposite the fluid conduit 40 is a mating fluid conduit 42 in housing 10 which continues the fluid communication from the surface 32 into the space 14 below reservoir 12. A liquid or gas-tight seal is provided between the conduits 40 and 42 by gasket 46 which fits into countersink 50 in boss 36. Alignment is aided by circular locating guide 44 which fits into circular recess 48. When the modules 4 and 6 are joined therefore, the pumped gas from pump 22 flows freely and without leakage from the pump 22 directly into the space 14 through conduits 40 and 42. Further, as shown in FIG. 8, even where there is no countersink and gasket an O-ring 45 will be used to provide a gas seal.

It will be evident from FIG. 2 that the configuration of the device shown in that figure has the boss 36 in recess 38 aligned off center from the centerlines of the modules 4 and 6. As illustrated in FIGS. 4 and 5, this necessitates that the radius of the matching flange 26a and groove 28a be less than the radius of the opposite flange and groove pair 26b/28b. Where the boss 36 and groove 38 are aligned centrally of the device, as in the embodiments shown in FIGS. 6–9, the radii of the flange and groove pairs at the opposite ends will be equal.

In the preferred configuration shown in FIG. 2, the battery 52 (here illustrated as a single AA or AAA 1.5 V battery) is disposed within the housing 10 of the reservoir module 4 and is connected to external contacts 54 by lead lines 56. Commonly, the contacts 54 and lead lines 56 will each be part of a single generally L-shaped strip of metal. When the modules 4 and 6 are coupled together, the contacts 54 are aligned with and in direct contact with contacts 58 in pump module 6, which in turn are electrically connected to the electronic components 24, such that the battery 52 then serves as the power source for the electronic components 24 and the pump 22.

The pump module 6 will, as described above, contain the pump 22, the conduit 40 for the gas generated by the pump, and the electrical circuitry 24 to operate the device. It is preferable that the electric current applied to the pump be maintained at a generally constant level. This is particularly true for devices for dispensing of medication, since the delivery rate of the medication must be kept constant at the level selected to avoid over- or under-dosing the patient. While the detrimental effects of significant amounts of current fluctuation are not as pronounced with non-medical devices, such as vapor scent emitters or "air fresheners," purchasers and users expect that the output of such a device will be reasonably uniform. A device which at various times emits large quantities of scent and at others emits little or none will not be well received in the marketplace.

Figure 10:
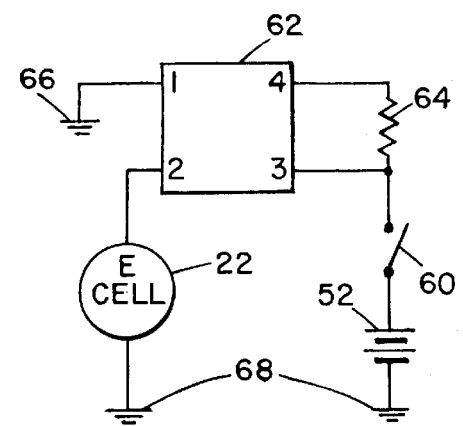
FIG. 10 is a schematic diagram of a basic electrical circuit for a pump module of the device of the present invention.

A simple electrical circuit for operation of a single pump rate device which yields a uniform current input at e-cell or pump 24 is illustrated in FIG. 10. The key components are the "e-cell" or pump 22, the battery or batteries 52 and a current rate control integrated circuit 62 which is regulated by resistor 64 and grounded by ground 66. The circuit in FIG. 10 is completed by a return group loop indicated as 68. An off-on switch 60 may optionally also be present, but the device may dispense with the switch if it is to run continually or if the off-on state is to be determined by connection to the battery 52. For instance, in the configuration shown in FIGS. 1–5, separation of the two modules 4 and 6 will halt the operation of pump 22 since the circuit will be opened by separation of contact pairs 54/58. A typical integrated circuit which is useful in this type of device is IC BCR (400 W;

Siemens Co.) used in connection with a 3 V total battery or battery group 52 output and a 140Ω resistor 64. A single 3 V battery may be used, or more preferably two 1.5 V batteries, such as two SR44 silver oxide batteries.

Figure 11:
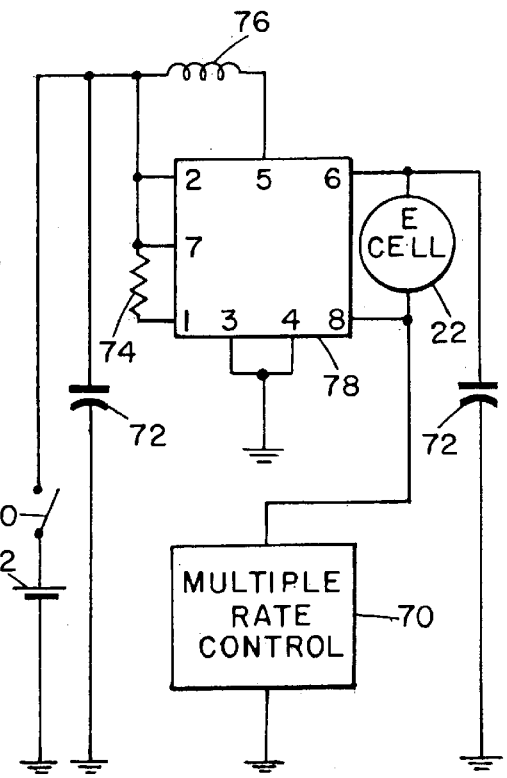
FIG. 11 is a schematic diagram of an electrical circuit for a pump module of the device of the present invention which incorporates a multiple rate flow control function.

FIG. 11 illustrates a more versatile circuit, one which permits the user to select from a plurality of predetermined power levels. This circuit is composed of the e-cell or pump 22, the battery or batteries 52, a manual rate controller 70 such as a variable resistor, step switch or the like. The voltage booster and current output regulation is provided by an integrated circuit 78 such as Maxim Co.'s MAX779. Capacitors 72 (here 100 $\mu$F) provide stabilization to the circuit by dampening voltage fluctuations and resistor 74 and inductor 76 determine the current outputs of the integrated circuit 78. The rate controller 70 protrudes through or is mounted on the surface 24 of pump module 6, where the device user can easily manipulate it to control the outlet gas flow rate at which the pump operates. Depending on the choice of rate controller 70, there can be continuous current level control over a range or a series of two or more specific step levels.

Electrical interconnections between the various electrical components, including the battery 52 and pump 22, can be by means of wires or printed circuits, or both, as appropriate.

The battery 52 can be one of various well known types of primary batteries, such as a mercury battery, manganese dioxide battery, aluminum-air battery or zinc-air battery. Air-actuated batteries, such as the aluminum-air battery or the zinc-air battery, or other batteries which produce power only when exposed to an activating agent, may be preferred if it is desired to dispense with the on/off switch 60 in the pump circuit.

The operation of the electrochemical pump or e-cell 22 is readily described. The battery 52 applies a voltage across an electrochemical cell which includes an ion exchange electrolytic membrane, preferably a perfluorosulfonic acid membrane coated with 90% platinum black/10% polytetrafluoroethylene, which sandwiched between a pair of material-previous electrodes, preferably titanium screens or porous titanium disks. As will be detailed further below, commonly atmospheric oxygen is drawn into the housing of module 6 (through openings not shown) in contact with the pump 24 and reduced in the presence of water in the electrochemical cell to provide electron transfer across the cell, regenerating pure oxygen from the water on the other side of the cell. The oxygen gas so formed passes through the exit conduits 40 and 42 and into space 14. In space 14 the resulting increasing of gas (oxygen) pressure acts against the bottom surface of the reservoir 12 and, as the gas volume and therefore pressure increases, it slowly compresses the reservoir 12 from below and gradually forces the liquid, vapor or gas within the reservoir out of the outlet port 16.

Details of the structure and function of the electrochemical cell are set out in U.S. Pat. Nos. 4,402,317 and 4,522,698 to Maget, both entitled "ELECTRO-CHEMICAL PRIME MOVER." The entire disclosures of those patents are incorporated herein by reference and thus need not be extensively repeated here. Suffice it to say that the voltage gradient established across the electrochemical cell reduces an electrochemically active material, such as atmospheric oxygen, at one electrode, by reacting with protons and electrons generated at the other electrode, while regenerating the gas molecules of the electrochemically active material, which are then evolved at the second electrode and pass through the conduits 40 and 42 into space 14, as described above. When the electrochemically active material is atmospheric oxygen or oxygen from some other source, the second electrode is conveniently called the oxygen evolution electrode. The water needed to support the action of an oxygen electrochemical cell may be supplied from a cellulosic or other water-retaining porous material located adjacent the oxygen evolution electrode. Alternatively there may be a water storage chamber 80 in the device, such as is shown in FIG. 8, from which a wick 82 extends into contact with the oxygen evolution electrode. The wick conveniently may be designed to at partially surround the conduit 40, and the storage chamber may be traversed by conduit 42, also as shown in FIG. 8. For low currents (e.g., <5 mA for a 1 cm$^3$ cell), the cell can operate satisfactorily without added water. For higher currents providing additional water increases the cell efficiency.

Typical specifications for devices of the embodiment of FIGS. 1–5 will be similar to those for the devices of FIGS. 6–7 set forth below, with the evident exception that since the battery or batteries 52 will be positioned in the reservoir module rather than the pump module, and may be one or more AA or AAA batteries rather than the watch/calculator (e.g. SR44) batteries, the external size, overall weight and weight distribution between the modules will reflect those different battery properties.

FIGS. 6–7 and 8–9 show two additional embodiments of device, in which like numbers designate like parts with reference to FIGS. 1–5. In the embodiment of FIGS. 6 and 7 the boss 36 and recess 38, with their included conduits 40 and 42, are centered laterally of the device, such that the radii of the coupling flanges 26a/26b and grooves 28a/28b are equal, and in joining the two modules, the device is rotated at the centerline rather than at a offset position as shown in FIG. 4. Further, FIG. 6 shows an embodiment where there are two batteries 52 to provide electrical power. As noted above, this configuration may be preferred when greater voltage is needed, but single batteries of the correct voltage do not exist, are larger in size than practical for use in the device, or are unduly expensive. This embodiment also illustrates the positioning of the battery 52 in the pump module, so that it is directly in the electrical circuit and external contacts 54/58 are not needed.

Typical specifications for a device of the type shown in FIGS. 6 and 7 are presented in the Table on the following page.

TABLE

| Assembly: | |
|---|---|
| Fluid volume | 10 ml, nominal |
| Size | 2.00" wide × 3.17" high × 0.55" deep (5.08 cm × 8.05 cm × 1.40 cm) |
| Weight | 1.85 oz (52.5 g), dry, with batteries |
| Rate range | >0 to 1 ml/hr |
| Reservoir sizes* | 5, 10, 20 ml |
| Pump Module: | |
| Usage | Reusable; no need for sterilization |
| Batteries | Two silver oxide, SR44** |
| Size | 2.00" wide × 1.45" high × 0.55" deep (5.08 cm × 3.68 cm × 1.40 cm) |
| Weight | 0.95 oz (26.9 g), with batteries |
| Current | Internally regulated |
| Fluid Reservoir | |
| Usage | Singe usage; can be sterilized |
| Size | 10 ml; 2.00" wide × 1.92" high × 0.55" deep (5.08 cm × 3.68 cm × 1.40 cm) |
| Weight | 0.90 oz (25.6 g), dry |
| Outlet port | 6" long microbore tubing with luer lock and |

TABLE-continued

| Fluid containment | non-vent cap Diaphragm bladder |
|---|---|

*Interchangeable reservoir sizes;
**May be changed with each reservoir change, or at greater intervals as appropriate)

Figure 9:
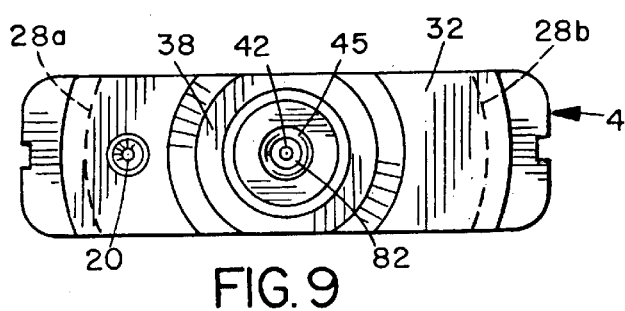
FIG. 9 is a bottom plan view of the reservoir module of the device of FIG. 8.

In the embodiment of FIGS. 8 and 9 there is shown the optional water chamber or reservoir 80 which provides water through wick 82 for the e-cell membrane, which provides the electrochemical reduction and regeneration of oxygen, as described above. The passage of conduits 40 and 42 through the wick 82, and the further passage of conduit 42 through the chamber 80 into the space 14 is also shown in FIGS. 8 and 9. It will be noted that the device of FIGS. 8 and 9 has the boss 36, recess 38 and chamber 80 centered laterally, although it will be understood that these can also be offset in the manner shown for the embodiment of FIGS. 1–5.

Typical specifications for devices of the embodiment of FIGS. 8–9 will be similar to those for the devices of FIGS. 6–7 set forth above, with the evident exception that external size, weight and weight distribution must include accommodation for the water reservoir 80 and wick 82.

While the embodiments shown in the Figures are of generally rectangular shape, it will be recognized that since the reservoir 12 is conformable to different shapes of the chamber 8, and that in most cases the electrical components in the pump module can be positioned is a variety of locations and connected with appropriate wiring, the devices can be constructed in a number of different external shapes. Of course, the critical limitation to this versatility is that the interface 32/34 between the two modules 4/6 must be such that the required coupling (as described herein) must be present, including alignment of the conduits 40/42, boss 36 and recess 38. Even with this limitation, however, the devices can be made, for instance, in shapes conformable to specific human or animal body surface areas, or in attractive shapes for use as air fresheners, and so forth.

As noted, a principal use of the present devices will be to dispense medication to humans or animals, for which use the outlet port 16 will be connected to or terminate in an appropriate transdermal medication device (as indicated at 17), such as a needle, cannula, absorbent patch, wound dressing, or the like. Any liquid, vaporous or vaporizable composition or gas medicament which is stable in the reservoir 8 over a reasonable service life, pumpable and which can be administered transdermally can used with the present device. For instance, one can administer medications or prophylactics specific to a particular disease, dysfunction or wound type, of for dispensing of therapeutic or prophylactic liquids to deal with specific problems, such as topical liquids to kill parasites on the surface of a human or animal patient or insecticide vapors. The device can also be used for dispensing such materials as human or animal hormones, birth control compositions, antibiotics and many other useful medications and treatment liquids.

In addition to use for dispensing medications or prophylactics to a human or animal patient, the devices of this invention may also be used to dispense chemicals, vapor forming liquids and their resulting vapors, for purposes such as air freshening, insert repelling, and the like. In such usage the liquid 18 is commonly vaporizable to provide a vapor which imparts a fragrance, provides an air cleaning or insect repellent function, or provides any other function for which vapors may be used. Depending on the liquid being used, the resulting vapors being dispersed from the device 2 can provide a pleasing fragrance (such as the fragrance of pine trees, flowers, etc.), serve as an air freshening or odor masking vapor, or disperse an insecticide into the ambient air. Volatile liquids which perform these functions are well known and readily available. One can also have the exterior of the device decorated in an attractively designed pattern and/or attractively finished on the surface, as with pictures of flowers, trees, attractive color patterns, and the like to enhance the appearance for use as an air freshener or scent producer in residences, offices and so forth. A smooth, easily cleanable surface will be preferred when the device is to be used for medication or prophyllatic delivery, so that the device will not be irritating when worn by the patient and will be easily wiped clean of body oils, fluids excreted from open wounds or sores, etc. for appearance and sanitation purposes.

It is evident that there will be numerous embodiments of this invention which, while not expressly described above, are clearly within the scope and spirit of the invention. The above description is therefore intended to be exemplary only, and the actual scope of the invention is to be determined solely from the appended claims.

We claim:

1. A fluid dispensing device comprising a reservoir module in a first housing, comprising an enclosed fluid containment chamber having an interior surface, a reservoir inlet port providing fluid communication from an exterior of said first housing to an interior of said chamber and a reservoir outlet port providing fluid communication from the interior of said chamber to the exterior of said device;

a pump module in a second housing, comprising a fluid pump, operating means for control and operation of said pump, and a pump fluid outlet port providing fluid communication from said pump to the exterior of said second housing;

coupling means for detachably joining said first housing containing said reservoir module and said second housing containing said pump module together and simultaneously separably aligning said reservoir inlet port and said pump fluid outlet port; and said alignment of said reservoir inlet port and said pump fluid outlet port creating fluid conduit means for providing fluid communication for a first fluid emerging from said pump to pass into said reservoir module and therein cause regulated expulsion of a second fluid within said reservoir through said outlet port, said reservoir inlet port and pump fluid outlet port cooperating with said coupling means to maintain said fluid conduit free from leakage of said first fluid during passage between said first housing containing said reservoir module and said second housing containing said pump module of said device.

2. A fluid dispensing device as in claim 1 wherein said pump is electrically driven and said operating means comprises electrical circuitry connected to said pump to provide electrical power to said pump.

3. A fluid dispensing device as in claim 2 wherein a battery comprises the source of said electrical power.

4. A fluid dispensing device as in claim 3 wherein said battery is disposed within said pump module of said device and connected directly to said electrical circuitry.

5. A fluid dispensing device as in claim 3 wherein said battery is disposed within said reservoir module of said device and connected to said electrical circuitry in said pump module through aligned electrical interconnection contacts disposed in opposed external surfaces of said pump module and said reservoir module, which respective contacts are brought into operational contact during interconnection of said modules by said coupling means.

6. A fluid dispensing device as in claim 1 wherein said fluid containment chamber is formed by a flexible fluid-impermeable film cooperating with at least a portion of said interior surface of said chamber.

7. A fluid dispensing device as in claim 1 wherein said fluid containment chamber comprises a bag.

8. A fluid dispensing device as in claim 1 wherein said fluid containment chamber is enclosed by at least one wall comprising a transparent material, such that a volume of fluid within said chamber can be observed visually.

9. A fluid dispensing device as in claim 1 wherein said pump is electrically driven and said operating means comprises electrical circuitry connected to said pump to provide electrical power to said pump.

10. A fluid dispensing device as in claim 9 wherein said operating means selectively provides a plurality of different power levels to said pump, such that said pump emits quantities of said pumped first fluid respectively proportional to said power levels selectively provided by said operating means, thus further providing respectively proportional quantities of said second fluid dispersed from said reservoir through said reservoir outlet port.

11. A fluid dispensing device as in claim 1 further comprising a plurality of different reservoir modules, each being configured with said coupling means, such that a single pump means may be coupled seriatim to each of said plurality of said reservoir modules.

12. A fluid dispensing device as in claim 1 further comprising external fluid conduit means attached to said reservoir outlet port for providing fluid communication for said second fluid dispensed from said reservoir outlet port to a device for administering said second fluid to a human or animal.

13. A fluid dispensing device as in claim 12 wherein said second fluid is a liquid having a therapeutic effect upon said human or animal.

14. A fluid dispensing device as in claim 1 wherein said second fluid is a gas or a vaporizable liquid.

15. A fluid dispensing device as in claim 14 wherein said second fluid is a gas and further comprising external fluid dispersion means attached to said reservoir outlet port for causing said gas dispensed from said reservoir outlet port to be dispersed into the ambient external environment.

16. A fluid dispensing device as in claim 14 wherein said second fluid is a vaporizable liquid and further comprising external fluid dispersion means attached to said reservoir outlet port for causing said liquid dispensed from said outlet port to vaporize and the resulting vapor to be dispersed into the ambient external environment.

17. A fluid dispensing device as in claim 1 wherein said pump is an electrochemical device which produces a gaseous output by electrolytic electron transfer between a reduced gas on an inlet side of said pump and a regenerated gas on an outlet side of said pump.

18. A fluid dispensing device as in claim 17 wherein said electrolytic electron transfer occurs across a membrane in which contained water participates electrochemically in said electron transfer.

19. A fluid dispensing device as in claim 18 further comprising a water reservoir separate from said fluid containment chamber, said water reservoir having fluid communication with said membrane and being the source of said water contained in said membrane.

20. A fluid dispensing device as in claim 19 wherein said water reservoir and said membrane are in fluid communication through a wick.

* * * * *